(12) United States Patent
Tustin

(10) Patent No.: US 7,253,304 B1
(45) Date of Patent: Aug. 7, 2007

(54) CARBONYLATION PROCESS

(75) Inventor: Gerald Charles Tustin, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/425,220

(22) Filed: Jun. 20, 2006

(51) Int. Cl.
C07C 67/36 (2006.01)
C07C 51/10 (2006.01)
C07C 51/54 (2006.01)

(52) U.S. Cl. ............... 560/232; 562/517; 562/890

(58) Field of Classification Search .......... 560/206, 560/207, 231, 232, 233; 562/517, 519
See application file for complete search history.

(56) References Cited

U.S. PATENT DOCUMENTS

| | | |
|---|---|---|
| 3,689,533 A | 9/1972 | Schultz |
| 3,717,670 A | 2/1973 | Schultz |
| 3,772,380 A | 11/1973 | Paulik et al. |
| 3,927,078 A | 12/1975 | Lapporte et al. |
| 4,046,807 A | 9/1977 | Kuckertz |
| 4,115,444 A | 9/1978 | Rizkalla |
| 4,252,741 A | 2/1981 | Porcelli et al. |
| 4,333,884 A | 6/1982 | Kubbeler et al. |
| 4,358,411 A | 11/1982 | Porcelli et al. |
| 4,366,259 A | 12/1982 | Knifton et al. |
| 4,374,070 A | 2/1983 | Larkins et al. |
| 4,417,077 A | 11/1983 | Drago et al. |
| 4,430,273 A | 2/1984 | Erpenbach et al. |
| 4,559,183 A | 12/1985 | Hewlitt |
| 4,629,809 A | 12/1986 | Vanderpool et al. |
| 5,003,104 A | 3/1991 | Paulik et al. |
| 5,144,068 A | 9/1992 | Smith et al. |
| 5,258,549 A | 11/1993 | Pimblett |
| 5,292,948 A | 3/1994 | Zoeller et al. |
| 5,298,586 A | 3/1994 | Beevor et al. |
| 5,380,929 A | 1/1995 | Erpenbach et al. |
| 5,416,237 A | 5/1995 | Aubigne et al. |
| 5,442,107 A | 8/1995 | Beevor et al. |
| 5,488,143 A | 1/1996 | Uhm et al. |
| 5,510,524 A | 4/1996 | Garland et al. |
| 5,900,505 A | 5/1999 | Tustin et al. |
| 5,922,911 A | 7/1999 | Jones et al. |
| 6,130,355 A | 10/2000 | Jones |
| 6,211,405 B1 | 4/2001 | Cheung et al. |
| 6,222,070 B1 * | 4/2001 | Bays et al. ............. 562/891 |
| 6,452,043 B1 | 9/2002 | Zoeller et al. |
| 6,667,418 B2 | 12/2003 | Broussard et al. |
| 6,916,951 B2 | 7/2005 | Tustin et al. |
| 7,115,774 B2 | 10/2006 | Magna et al. |

FOREIGN PATENT DOCUMENTS

| | | |
|---|---|---|
| DE | 3107518 | 12/1981 |
| EP | 0008396 A1 | 5/1980 |
| EP | 0081152 | 6/1983 |
| EP | 0109212 | 5/1984 |
| EP | 0087870 | 4/1985 |
| EP | 0096974 | 9/1985 |
| EP | 0153834 | 9/1985 |
| EP | 0087869 | 7/1986 |
| EP | 0338730 | 10/1989 |
| EP | 0391680 | 10/1990 |
| EP | 0584964 | 3/1994 |
| EP | 0752406 | 1/1997 |
| EP | 0976711 | 2/2000 |
| GB | 2029409 | 3/1980 |
| JP | 146933 | 5/2003 |
| WO | 99/54273 | 10/1999 |

OTHER PUBLICATIONS

Wasserscheid, Peter and Keim, Wilhelm, 'Ionic Liquids—New "Solutions" for Transition Metal Catalysis', Angew. Chem. Int. Ed., 2000, 39, pp. 3772-3789.
Howard, et al, Catalysis Today, 18, (1993) pp. 325-354.
Fujimoto et al, Chemistry Letters (1987) pp. 895-898.
Fujimoto et al, Journal of Catalysis, 133, (1992) pp. 370-382.
Welton, Chemical Reviews 99 (1999) pp. 2071-2083.
Knifton, J. Catal., 96, (1985) pp. 439-453.
Mizushima et al, Green Chemistry 3 (2001) pp. 76-79.
Chauvin et al, Chem. Int. Ed. Engl. 34 (1995) pp. 2698-2700.
Yagita et al, Catalysis Letters, 2 (1989) pp. 145-148.
Riisager et al, "First application of supported ionic liquid phase (SILP) catalysis for continuous methanol carbonylation", Chem. Commun., 2006, pp. 994-996.
W. Bertloff, Carbonylation, Ulmann's Encyclopedia of Industrial Chemistry 6th Edition, vol. 6, Wiley-VCH Verlag GmbH & Co., KGaA, Weinheim, Germany, p. 473 (2003).
W. Rienmenschneider, "Carboxylic Acids, Aliphatic", Ulmann's Encyclopedia of Industrial Chemistry, 6th Edition, vol. 6, Wiley-VCH Verlag GmbH & Co, KGaA, Weinheim, Germany, p. 493 (2003).
Yoneda et al, "Recent advances in processes and catalysts for the production of acetic acid", Applied Catalysis A: General 221 (2001) 253-265.
De Blasio et al, "Activity and Stability of Two Polymer-Supported Rhodium-Based Catalysts for the Vapour Phase Carbonylation of Methanol", Journal of Catalysis 176, (1998) 253-259.
Sunley et al, "High productivity methanol carbonylation catalysis using iridium The Cativa (TM) process for the manufacture of acetic acid", Catalysis Today 58 (2000) 293-307.

(Continued)

Primary Examiner—Karl Puttlitz
(74) Attorney, Agent, or Firm—Eric D. Middlemas; Bernard J. Graves, Jr.

(57) ABSTRACT

Disclosed is a carbonylation process wherein a mixture of a dialkyl carbonate and halide compound is contacted with carbon monoxide in the presence of a metal selected from Group VIII of the Periodic Table to co-produce carbon dioxide and a carbonyl compound selected from a carboxylic acid, an alkyl carboxylate ester, a carboxylic acid anhydride or a mixture of any two or more thereof. The carbon dioxide co-product of the process may be recovered, and sold or further reacted with a suitable substrate to produce useful chemicals such as urea or cyclic carbonates.

22 Claims, No Drawings

OTHER PUBLICATIONS

Zhao, et al, "Ionic liquids: applications in catalysis", Catalysis Today 74 (2002) 157-189.

Riisager et al, "Very Stable and Highly Regioselective Supported Ionic-Liquid-Phase (SILP) Catalysis: Continuous-Flow Fixed-Bed Hydroformylation of Propene", Angew. Chem. Int. Ed. 2005, 44,815-819.

Mehnert, "Supported Ionic Liquid Catalysis", Chem. Eur. J. 2005, 11, 50-56.

Riisager, et al, "Supported Ionic Liquid Phase (SILP) Catalysis: An Innovative Concept for Homogeneous Catalysis in Continuous Fixed-Bed Reactors", Eur. J. Inorg. Chem. 2006, 695-706.

Drago, et al, "Ionic Attachment as a Feasible Approach to Heterogenizing Anionic Solution Catalysts, Carbonylation of Methanol", American Chemical Society (1981) vol. 20, No. 3, 641-644.

Haynes et al, "Structure and Reactivity of Polymer-Supported Carbonylation Catalysts", J. Chem. Soc., Dalton Trans., 2002, 2565-2572.

Welton, "Ionic Liquids in Catalysis", Coordination Chemistry Reviews 248 (2004) 2459-2477.

Riisager et al, "Stability and Kinetic Studies of Supported Ionic Liquid Phase Catalysts for Hydroformylation of Propene", Ind. Eng. Chem. Res. 2005, 44, 9853-9859.

Danish application titled "A process for continuous carbonylation by supported ionic liquid-phase catalysis" (Unpublished patent application provided by inventor and believed to be related to Denmark Patent Application No. 2005/00735, filed May 20, 2005, and PCT application Serial No. PCT/DK2006/000275).

* cited by examiner

CARBONYLATION PROCESS

FIELD OF THE INVENTION

This invention pertains to a process for the preparation of carboxylic acids and/or derivatives thereof. More specifically, this invention pertains to a process wherein a mixture of a dialkyl carbonate and halide compound is contacted with carbon monoxide in the presence of a metal selected from Group VIII of the Periodic Table. The carbon dioxide co-product of the process may be reacted with a suitable substrate to produce useful chemicals such as urea or cyclic carbonates.

BACKGROUND OF THE INVENTION

It is known that carboxylic acids and carboxylic acid derivatives may be produced by the carbonylation of a mixture of (1) a carbonylation feedstock compound such as alcohols, esters, ethers or mixtures thereof and (2) a halide compound such as hydrogen iodide and/or an alkyl iodide. The products of these known processes are carboxylic acids, esters and/or anhydrides, depending on the specific feedstock and processes conditions employed. Carboxylic esters and anhydrides are the primary products when water is absent, whereas carboxylic acids and esters are the main products when water is present. The most efficient catalysts for these reactions are metals from Group VIII of the Periodic Table. Thus carbonylation of mixtures of methanol and a halide compound produces acetic acid, and methyl acetate and water also may be produced at low methanol conversion. Carbonylation of mixtures of methyl acetate and a halide compound produces acetic anhydride in the absence of water.

The use of dimethyl ether (DME—also referred to as methyl ether) as the feedstock compound in carbonylation processes produces methyl acetate and acetic anhydride at sufficiently high rates of conversion in the absence of water. DME is an attractive feedstock material for acetic anhydride synthesis because the recycle of acetic acid equivalents through the carbonylation reactor is greatly reduced. Although DME is an attractive feedstock material for the synthesis of acetic acid and derivatives in some ways, it has limitations due to its physical properties. For example, the boiling point of DME is −24° C. at atmospheric pressure. Therefore, DME either must be stored in special pressure vessels or in refrigerated vessels. Either of these options is expensive. An accidental release of dimethyl ether into the environment may result in a fire or an explosion. An alternative carbonylation feedstock compound is needed which avoids high recycle of acetyl equivalents and the troublesome physical properties of DME.

BRIEF SUMMARY OF THE INVENTION

I have found that carboxylic acids and derivatives thereof and carbon dioxide may be produced by the carbonylation of dialkyl carbonates. The present invention thus provides a process for the co-production of carbon dioxide and a carbonyl compound selected from a carboxylic acid, an alkyl carboxylate ester, a carboxylic acid anhydride or a mixture of any two or more thereof which comprises contacting in a carbonylation zone a dialkyl carbonate with carbon monoxide in the presence of a metal carbonylation catalyst and a halide compound under carbonylation condition of pressure and temperature. The carbon dioxide produced at the reaction pressure may be reacted with a suitable substrate to produce useful chemicals such as urea or cyclic carbonates or recovered and sold.

The carbonylation process of the present invention is especially useful for the co-production of carbon dioxide and an acetyl compound selected from acetic acid, methyl acetate, acetic anhydride and mixtures of any two or more thereof using dimethyl carbonate as the feedstock material. Dimethyl carbonate, unlike dimethyl ether, has a relatively high boiling point (90° C.) at atmospheric pressure. Hence, dimethyl carbonate is much easier and safer to handle than dimethyl ether. Dimethyl carbonate also has high potential for use as an octane enhancer, solvent and phosgene replacement and, therefore, may become available in very large quantities at low cost. The availability of large quantities of dimethyl carbonate at low cost enhances its potential utility as a starting material for the economical preparation of acetyl derivatives via carbonylation.

The present invention co-produces a carbonyl compound and carbon dioxide which may be converted into useful chemicals or recovered and sold. Since the carbonylation reaction is typically operated at elevated pressure, the carbon dioxide also is generated at elevated pressure. The high pressure carbon dioxide generated by the carbonylation process may then be used to convert epoxides into valuable cyclic carbonates at pressures in the range of the carbon dioxide pressures generated by the process of the invention. The cyclic carbonates are useful solvents and monomer materials for polymeric polycarbonates. The high pressure carbon dioxide generated by the present process also may be converted into nitrogen derivatives such as urea by reaction with ammonia or an amine. Ureas have utility as fertilizers and as polymer intermediates. An illustration of the utility of the invention is the co-production of methyl acetate and urea entirely from synthesis gas, oxygen and nitrogen. This is illustrated by the following series of reactions:

Methanol synthesis: $2CO+4H_2=2CH_3OH$ (1)

Ammonia synthesis: $3H_2+N_2=2NH_3$ (2)

Dimethyl carbonate synthesis: $2CH_3OH+\frac{1}{2}O_2+CO= (CH_3O)_2CO+H_2O$ (3)

Methyl acetate synthesis: $(CH_3O)_2CO+CO=CH_3O(O)CCH_3+CO_2$ (4)

Urea synthesis: $2NH_3+CO_2=(NH_2)_2CO+H_2O$ (5)

Net reaction: $4CO+7H_2+\frac{1}{2}O_2+N_2=CH_3O(O)CCH_3+ (NH_2)_2CO+2H_2O$ (6)

DETAILED DESCRIPTION

The alkyl groups of the dialkyl carbonate feedstock material may contain 1 to about 20 carbon atoms. The alkyl groups may be substituted with groups inert under the process reaction conditions (non-reactive groups) such as aryl groups, e.g., phenyl. The two alkyl substituents of the dialkyl carbonate feedstock may be the same or different. It is preferable that the two carbonate alkyl groups are the same. Dimethyl carbonate is the most preferred carbonate. The dialkyl carbonate feedstock may be carbonylated with one equivalent of carbon monoxide to produce an alkyl carboxylate ester of the carboxylic acid derived from the from the alkyl group of the dialkyl carbonate and carbon dioxide (reaction 4 above). The dialkyl carbonate feedstock may be carbonylated with two equivalents of carbon mon oxide to produce an anhydride of the carboxylic acid derivable from the alkyl group or groups of the dialkyl carbonate. Thus, dimethyl carbonate may be carbonylated with one carbon monoxide molecule to produce methyl acetate and carbon dioxide (reaction 4 above) or with two carbon monoxide molecules to produce acetic anhydride (reaction 7) and carbon dioxide:

Acetic anhydride synthesis: $(CH_3O)_2CO + 2CO = CH_3C(O)O(O)CCH_3 + CO_2$     (7)

When dimethyl carbonate is carbonylated in the presence of water and/or methanol, acetic acid also may be produced. The process may be operated to produce mixtures of products. Thus, dimethyl carbonate may be contacted with carbon monoxide in the presence of methanol or water to produce mixtures comprising methyl acetate, acetic anhydride and acetic acid.

The carbonylation process of the present invention may be operated as a vapor or liquid phase process. In the liquid phase process, the catalyst components are dissolved in a solution typically comprising the feedstock material or materials, products and halide compound and may contain additional liquid components. The liquid phase process may be operated either in a batch mode or a continuous mode with the continuous mode being preferred. In vapor phase operation, the catalyst may be a supported catalyst comprising a metal carbonylation catalyst deposited on an inert support material. Alternatively, the catalyst in vapor phase operation may be a metal carbonylation catalyst compound dissolved in a relatively non-volatile (non-volatile under the carbonylation conditions of pressure and temperature) liquid. Vapor phase operation typically is carried out in a continuous mode of operation wherein the vapor feedstock materials contact the catalyst mixture and the products are removed from the carbonylation zone as a vapor. Carbon is an example of a catalyst support material for vapor phase operation. Molten ammonium, phosphonium and sulfonium salts, typically halides, are examples of non-volatile liquids useful in vapor phase operation. The molten ammonium, phosphonium and sulfonium salts also may be used in the liquid phase operation as solvent components. A carboxylic acid also may be used as a component of the liquid or vapor phase processes, although it can be incorporated in the product if a dialkyl carbonate other than dimethyl carbonate is used. When acetic acid is used as a component in the carbonylation of dimethyl ether, methyl acetate and methanol also may be produced, but this reaction does not represent a net production of acetyl since no carbonylation has occurred. It is preferable to perform the liquid phase in a purged mode so the carbon dioxide produced can leave the reactor.

The carbonylation process of the present invention may be performed at elevated temperatures ranging from about 100 to 300° C. Liquid phase carbonylation is performed at a lower temperature than the vapor phase reaction. Typical temperatures for liquid phase operation range from about 100 to 220° C. with temperatures of about 150 to 200° C. being preferred. Higher temperatures are preferred for the vapor phase operation wherein the catalyst is a catalytic carbonylation metal deposited on an inert support. For example, the process may be carried out in the vapor phase at temperature of about 150 to 300° C. with temperatures of about 170 to 250° C. being preferred. The upper temperature for vapor phase process using a relatively non-volatile liquid such as a molten ammonium, phosphonium or sulfonium salt is about 250° C., preferably about 230° C.

The carbonylation process may be operated at a total pressure between about 0.1 and 500 bars absolute (bara). The pressure depends on the particular dialkyl carbonate employed, the mode of operation (vapor or liquid phase) and on the Group VIII metal catalyst selected. Higher pressures are required for less active catalysts such as cobalt. The preferred catalysts for the reaction comprise rhodium or iridium and compounds thereof which may be utilized at total pressures between about 0.1 and 100 bara, preferably between 1 and 80 bara, and most preferably between about 3 and 70 bara. When operating in the liquid phase the pressure is at a level sufficient to maintain the liquid feedstock materials and products in the liquid state at the process temperature employed, to maintain the catalyst in its active state and to provide adequate mass transfer. For example, pressures between about 10 and 70 bara may be used in liquid phase operation. When operated in the vapor phase the process normally is performed at pressures lower than the pressure used in liquid phase operation. The lower pressure required for vapor phase operation is a result of the need to maintain the reactants and products in the vapor phase at the process temperature. The pressures for vapor phase operation typically range from about 1 to 50 bara, preferably between about 3 to 30 bara.

The carbon monoxide employed in the process of the present invention may be purified carbon monoxide or carbon monoxide containing other gases. The carbon monoxide need not be of high purity and may contain from about 1% by volume to about 99% by volume carbon monoxide, preferably from about 70% by volume to 99% by volume carbon monoxide. The remainder of the gas mixture may comprise such gases as nitrogen, hydrogen, water and parafinic hydrocarbons having from 1 to 4 carbon atoms. Although not part of the reaction stoichiometry of the carbonylation process, hydrogen may be useful in maintaining optimal catalyst activity. Therefore, the preferred ratio of carbon monoxide to hydrogen is in the range of 99:1 to 2:1 by volume, although mixtures containing higher hydrogen levels may be used. If the desired product is a carboxylic anhydride, the amount of water in the carbon monoxide feed should be minimized. The amount of carbon monoxide fed to the carbonylation zone provides a carbon monoxide: dialkyl carbonate molar ratio of about 0.1:1 to 1,000:1, preferably about 0.5:1 to about 100:1 and most preferably about 1:1 to 20:1.

The carbonylation catalyst employed in the process of the invention comprises one or more transition metals selected from Group VIII (Fe, Co, Ni, Ru, Rh, Pd, Os, Ir, Pt) of the Periodic Table. The form of the Group VIII metal is not critical. Non-limiting examples of Group VIII metal compounds which may be used include those containing halide, trivalent nitrogen, organic compounds of trivalent nitrogen, carbon monoxide, hydrogen, carboxylate and 2,4-pentanedione, either alone or in combination. Many of these metal compounds are commercially available. Examples of suitable Group VIII species include, but are not limited to, rhodium trichloride hydrate, iridium trichloride hydrate, nickel iodide hydrate, palladium acetate and palladium chloride. Preferred Group VIII metal species include Rh, Ir, Ni, Co and Pd separately or in combination and the combination of Ir with Ru, Os, Pd or Pt promoters. Other promoters suitable for use with Ir include compounds of Ga, In, Cd, Hg, Re, W and Mo. More preferred Group VIII metal species comprise Rh, Ir and Pd and the combination of Ir with Ru, Os, Pd or Pt. When Ru, Os, Pd or Pt are used as promoters with Ir, the promoter/Ir molar ratio preferably ranges from about 0.1 to 15, more preferably from about 0.5 to 10. When water is absent from the carbonylation zone, the most preferred Group VIII metal carbonylation catalyst comprises Rh and compounds of Rh. When water is present, the Group VIII metal carbonylation catalyst may be either Rh or promoted Ir. The amount or concentration of the Group VIII metal may vary considerably depending on a number of variables such as the identity of the Group VIII metal or metals, the dialkyl carbonate employed, other reactants present, the carbonylation conditions utilized and the mode of operation (liquid phase or vapor phase). When of the carbonylation process is operated using the preferred dimethyl carbonate under anhydrous conditions operating in the liquid phase, the concentration of rhodium in the carbonylation zone may be about 250 to 1300 ppm, preferably about 500 to 1000 ppm. For vapor phase operation using one or more Group VIII metals supported on a catalyst support material such as carbon, the amount of catalytic metal on the catalyst support may be about 0.01 and 10% based on the weight of the supported catalyst. The amount of metal on the supported catalyst preferably is about 0.05 to 5 weight percent, most preferably abut 0.1 and 2 weight percent (same basis). For vapor phase operation of the process employing a nonvolatile liquid (such as an ionic liquid, e.g., an ammonium, phosphonium or sulfonium salt), the concentration of rhodium in the carbonylation zone may be about 0.0001 and 1.0 molar, preferably between about 0.001 and 0.5 molar and more preferably between about 0.005 and 0.25 molar. When using the preferred dimethyl carbonate feedstock with a nonvolatile ionic liquid 1-butyl-3-methylimidazolium iodide in vapor phase operation, the concentration of Rh metal in the carbonylation zone may be about 0.005 to 0.05 molar.

The carbonylation process of the present invention employs a halide selected from chlorine, bromine and iodine compounds. Examples of halides include hydrogen halides such as hydrogen iodide and gaseous hydroiodic acid; alkyl and aryl halides containing up to about 20 carbon atoms such as methyl iodide, ethyl iodide, 1-iodopropane, 2-iodobutane, 1-iodobutane, methyl bromide, ethyl bromide, benzyl iodide and mixtures thereof. The halide compound preferably is a hydrogen halide or an alkyl halide having up to about 6 carbon atoms. Non-limiting examples of preferred halides include hydrogen iodide, methyl iodide, hydrogen bromide, methyl bromide and mixtures thereof. The halide also may be a molecular halogen such as $I_2$, $Br_2$ or $Cl_2$. The most preferred halides are iodides, e.g., hydrogen iodide and alkyl iodides containing up to about 6 carbon atoms. The alkyl residue of the alkyl iodide preferably is the same as the alkyl residues of the dialkyl carbonate feedstock. Non-limiting examples of the most preferred volatile halides include methyl iodide, hydrogen iodide and molecular iodine. The amount of halide present in or fed to the carbonylation zone can vary substantially and typically provides a molar ration of equivalents of dialkyl carbonate to halide compound of about 1:1 to 10,000:1, preferably about 5:1 to about 1000:1.

The carbonylation process may be facilitated by the addition of ionic species, i.e., salts, to the carbonylation zone, especially when the Group VIII metal catalyst is rhodium, although the use of such salts is not essential. The salts are beneficial both in the presence or absence of water in the carbonylation zone. The ionic species may be a salt of an alkali, alkaline earth, transition or other metal. The salt also may be an ammonium, phosphonium or sulfonium salt which also may function as a non-volatile reaction medium as described above. Lithium and chromium salts are preferred. Normally, the anion of the salt is a halide that is the same as the halide of the halide compound described above or the anion, i.e., the carboxylate ion, of the carboxylic acid produced. When the process is carried out using the preferred dimethyl carbonate under anhydrous conditions in the liquid phase, the concentration of lithium typically is about 175 to 5000 ppm based on the total weight of the contents of the carbonylation zone. Lithium concentrations of about 1500 to 3700 ppm (same basis) are preferred. For vapor phase operation using rhodium supported on carbon, the atomic ratio of lithium to rhodium typically is about 0.1 to 100, preferably about 1 to 10, more preferably about 2 to 8. For vapor phase processes employing a nonvolatile ionic liquid the molten salt normally is the solvent.

The carbonylation processes described herein may further comprise recovery of the co-produced carbon dioxide for sales or for use as a feedstock for the production of useful chemicals such as, for example, urea or cyclic carbonates. In one embodiment of the invention, for example, in a liquid phase process, the liquid carbonylation product effluent can be removed from the carbonylation zone and fed to an evaporator wherein the liquid product is separated into a vapor fraction and a liquid fraction. In the evaporator, the pressure generally is reduced and partial vaporization occurs. The vapor fraction will typically comprise carbon dioxide, unreacted carbon monoxide, the carbonylation products, and other low boiling components such as, for example, methyl iodide, methyl acetate and/or dimethyl ether. The liquid fraction typically will comprise a solution of catalyst or catalyst components in the carbonylation product, for example, in the carboyxlic acid, alkyl carboxylate ester, or carboxylic anhydride product, and small amounts of various high boiling impurities and tars. The liquid fraction, generally, will be recycled to the carbonylation zone and the vapor fraction separated into its component parts by a series of distillations.

Similarly, for a vapor phase process, the vapor carbonylation product effluent can be recovered and condensed into liquid and vapor fractions. The liquid fractions typically will comprise the carbonylation product and halide compounds used in the carbonylation reaction. The vapor fraction, containing the coproduced carbon dioxide and unreacted carbon monoxide may be subjected to the carbon dioxide removal and recovery as described herein.

The non-condensed gaseous components of the vapor fraction, comprising the coproduced carbon dioxide and unreacted carbon monoxide, can be passed to a carbon dioxide removal and recovery step. The carbon monoxide which remains in the vapor fraction after removal and recovery of the carbon dioxide can be recycled back to the carbonylation zone. Removal and recovery of carbon dioxide may comprise any of a number of methods known in the art. The carbon dioxide in the vapor fraction may be recovered by chemical absorption methods, exemplified by contacting the carbon dioxide in the vapor fraction with caustic soda, potassium carbonate or other inorganic bases, or alkanol amines. Examples of suitable alkanolamines for the present invention include primary and secondary amino alcohols containing a total of up to 10 carbon atoms and having a normal boiling point of less than about 250° C. Specific examples include primary amino alcohols such as monoethanolamine (MEA), 2-amino-2-methyl-1-propanol (AMP), 1-aminobutan-2-ol, 2-amino-butan-1-ol, 3-amino-3-methyl-2-pentanol, 2,3-dimethyl-3-amino-1-butanol, 2-amino-2-ethyl-1-butanol, 2-amino-2-methyl-3-pentanol, 2-amino-2-methyl-1-butanol, 2-amino-2-methyl-1-pentanol, 3-amino-3-methyl-1-butanol, 3-amino-3-methyl-2-butanol, 2-amino-2,3-dimethyl-1-butanol, and secondary amino alcohols such as diethanolamine (DEA), 2-(ethylamino)-ethanol (EAE), 2-(methylamino)-ethanol (MAE), 2-(propylamino)-ethanol, 2-(isopropylamino)-ethanol, 2-(butylamino)-ethanol, 1-(ethylamino)-ethanol, 1-(methylamino)-ethanol, 1-(propylamino)-ethanol, 1-(isopropylamino)-ethanol, and 1-(butylamino)-ethanol.

Alternatively, the carbon dioxide in the vapor fraction may be removed by physical absorption methods. Examples of suitable physical absorbent solvents are methanol and other alkanols, propylene carbonate and other alkyl carbonates, dimethyl ethers of polyethylene glycol of two to twelve glycol units and mixtures thereof (commonly known under the trade name of Selexol™ solvents), n-methyl-pyrrolidone, and sulfolane. Physical and chemical absorption methods may be used in concert as exemplified by the Sulfinol™ process using sulfolane and an alkanolamine as the absorbent, or the Amisol™ process using a mixture of an alkanolamine and methanol as the absorbent.

The absorbed carbon dioxide may be recovered by heating the absorption solvent and compressing the released carbon dioxide. The compressed carbon dioxide may then be sold or used for chemical production.

EXAMPLES

The operation of the carbonylation of the present invention is further illustrated by the following examples wherein all percentages are by weight unless specified otherwise.

Stability Evaluation—This example illustrates a preliminary test to determine if acetic acid, lithium iodide and methyl iodide cause uncontrolled decomposition of dimethyl carbonate. The example further illustrates the liquid phase carbonylation of dimethyl carbonate to methyl acetate. Stability test—Acetic acid (21.0 g, 0.35 mole) was added to dimethyl carbonate (81.1 g, 0.9 mole) in a 250 mL flask at ambient temperature. The mixture remained at ambient temperature and no gas evolution was observed. Lithium iodide (2.67 g, 0.02 mole) then was added, and the mixture warmed slightly as the LiI dissolved with no significant gas evolution. When methyl iodide (14.2 g, 0.1 mole) was added no heat or gas evolution was observed. The flask was tightly stoppered and left overnight at ambient temperature overnight. The stopper was still tightly in the flask the next morning indicating that no significant gas evolution had occurred. The weight of the stoppered flask was 253.08 g. The flask was fitted with a reflux condenser, and the mixture was refluxed for 7 hours. After cooling, the flask containing the mixture was stoppered with the original stopper and weighed again. The final weight was 251.60 g indicating a weight loss of only 1.48 g. This preliminary stability test illustrates that there is essentially no carbon dioxide evolution in the presence of the normal reagents but in the absence of the rhodium catalyst and carbon monoxide at elevated temperature.

Example 1

This example illustrates the production of methyl acetate by liquid phase carbonylation using dimethyl carbonate as the feedstock. Acetic acid (21.0 g, 0.35 mole), dimethyl carbonate (81.1 g, 0.9 mole), methyl iodide (14.2 g, 0.10 mole) lithium iodide (2.67 g, 0.02 mole) and rhodium trichloride hydrate (63 mg, 40.01% Rh, 0.25 mmole) were charged to a 300 mL, stirred autoclave constructed of Hastelloy alloy. The autoclave was fitted with a gas dispersion device, a chilled reflux condenser, a back pressure regulator and a feed gas flow controller. The condenser was set for 5 to 10° C., the mixture pressurized to 69 bar gauge (barg) with a hydrogen/carbon monoxide gas mixture consisting of 5 volume % hydrogen/95 volume % carbon monoxide, and the gas flow rate set for 0.5 mole/hour. The apparatus was vented to the atmosphere and re-pressurized to 24 barg with 5 volume % hydrogen/95 volume % carbon monoxide. The stirrer was started and the apparatus was heated to 160° C. with a purge rate of 0.5 mole gas/hour. After the apparatus had reached 160° C., the pressure was adjusted to 55 barg while feeding the hydrogen/carbon monoxide gas mixture at 0.5 mole/hour. The reaction was continued at 160° C. at 55 barg while feeding the hydrogen/carbon monoxide gas mixture at 0.5 mole/hour for 5 hours. The reactor then was cooled and then vented.

The crude product mixture (83.62 g) was recovered from the autoclave and analyzed by two gas chromatography programs. The first program analyzed for methyl iodide, methyl acetate, methanol, dimethyl carbonate, water and acetic acid and used a Hewlett Packard Model 6890 gas chromatograph fitted with a 30 m×0.25 mm DB-FFAP capillary column (0.25 micron film thickness) programmed at 40° C. for 5 minutes, 25° C./minute to 240° C. and holding at 240° C. for 1 minute using a thermal conductivity detector held at 250° C. (injector temperature=250° C.). Mixtures were prepared for gas chromatographic analysis by adding 5 mL of tetrahydrofuran solution containing 2% decane internal standard to an accurately weighed 1 gram sample of the product mixture. The second program analyzed for methyl iodide, acetone, methyl acetate, dimethyl carbonate, acetic acid, acetic anhydride and ethylidene diacetate: an accurately-weighed one-gram sample was diluted with 5 mL of an internal standard solution prepared from dilution of 20 mL p-xylene to 500 mL with acetonitrile. One microliter of this mixture was injected onto a 30M×0.25 mm×0.25 micron DB 1701 column under the following conditions using 14.5 pounds per square inch gauge (psig−1 barg) helium carrier gas flowing at 3.0 mL/minute. Injector parameters: T=250° C., split flow=100 mL/minute, split ratio=75:1, purge=2 mL/minute; Detector parameters: flame ionization, T=250° C.; Oven parameters: 3 minutes at 35° C., 15° C./minute to 250° C., 250° C. for 0 minutes. The crude product mixture contained 9.07% methyl iodide, 0.19% acetone, 65.8% methyl acetate, 0.01% dimethyl carbonate, 4.5% methanol, and 7.3% acetic acid. The net production of acetyl was 0.495 moles (moles of methyl acetate present−moles of acetic acid consumed).

Example 2

This example illustrates the formation of methyl acetate and carbon dioxide over a heterogeneous catalyst in the vapor phase. The reactor used in this example was constructed entirely of Hastelloy C alloy. Vaporized reactants entered the base of the reactor via a 0.375 inch (9.5 mm) outer diameter (O.D.) inlet tube having a wall thickness of 0.065 inch (1.65 mm). The portion above the inlet tube expanded as a collar piece as a cone into a cylindrical section having a 0.625-inch (1.6 cm) inner diameter (I.D.) and a wall thickness of 0.1875 inch (4.8 mm) with overall length of 2.00 inches (5.1 cm). The top 0.38-inch (9.6 mm) portion of the collar was machined to a diameter of 0.750 inch (1.9 cm). The machined portion of the collar contained a 0.735-inch (1.87 cm) diameter by 0.0625-inch (1.65 mm) thick 5 micron metal filter (Hastelloy C) which acted as a gas dispersion device and support for catalyst. The filter and the collar containing the filter were welded to a 6.25-inch (15.9 cm) long by 0.625-inch (1.6 cm) I.D./0.750-inch ((1.9 cm) O.D. reaction tube (Hastelloy C). The reaction tube was welded to an expanded zone increasing in a conical fashion at 45° to an outer diameter of 1.50 inches (3.81 cm), continuing in a cylindrical fashion for another 1.83 inches (4.56 cm) and then decreasing at a 45° angle and welded to a 4.50 inch (11.4 cm) long by 0.375-inch (0.95 cm) O.D. loading and sensing tube. The vertical loading and sensing tube contained a 0.375-inch (0.95 cm) O.D. pressure transducer side arm located 2.0 inches (5.1 cm) above the expanded zone and positioned at 45° from vertical of the loading and sensing tube. Vapor product was removed from the expanded zone through a 0.125 inch (3.18 mm) O.D. product removal line which extended up to approximately half the vertical distance of the expanded zone and off to one side. A 5 micron sintered metal filter (Hastelloy C) was welded to the top end of the product removal line. The product removal line exited the expanded zone through the bottom conical portion of the expansion zone and continued downward to a distance past the base of the reactor inlet line.

Metered gas flows were maintained by Brooks 5850 Series E mass flow controllers interfaced with a Camile® 3300 Process Monitoring and Control System. Temperature control also was provided by the Camile® 3300 Process Monitoring and Control System. Liquid feed was provided by an Alltech 301 HPLC pump. Liquid and gas feeds were fed to a heated Hastelloy C vaporizer maintained at 240° C. and transported through a transfer line at 240° C. to the base of the reactor inlet tube. Heat to the reactor was provided by three separate split aluminum blocks with each split aluminum block surrounded by band heaters. Each split aluminum block heating unit had its own temperature control provided by the Camile® 3300 Process Monitoring and Control System. The bottom heater provided heat to the reactor inlet tube and collar piece. The central heater provided heat to the reaction tube section. The top heater provided heat to the expansion zone. A thermowell (Hastelloy C) extending from the top of the reactor to the gas dispersion frit allowed for monitoring the catalyst temperature at various locations inside the reactor.

The end of the product removal line was connected to a condenser (Hastelloy C), which was attached to a product collection tank (Hastelloy C) with a working capacity of one liter. The pressure was maintained using a Tescom Model 44-2300 backpressure regulator attached to a vent line on the top of product collection tank. Liquid samples were collected from a valve at the base of the liquid collection tank. Liquid products from the collection tank were weighed and analyzed by gas chromatography as described in Example 1.

The reactor was loaded with the carbon-supported catalyst (10 mL, 4.1 g) containing 0.6% Rh with lithium promoter (LiI–Li/Rh atomic ratio=4). The reactor was pressurized to 14 barg with carbon monoxide and the carbon monoxide flow was set for 150 standard cubic centimeters per minute (SCCM). The reactor was heated to 190° C. A liquid mixture containing a molar ratio=1.0 dimethyl carbonate/0.33 acetic acid/0.084 methyl iodide (density=1.09 g/mL) was fed to the vaporizer at 0.14 mL/minute along with the carbon monoxide. The catalyst bed temperature rose and eventually leveled out at 198° C. A sample of the condensate (9.9 g) taken after 2 hours contained the following components: 5.58% methyl iodide, 33.88% methyl acetate, 4.84% dimethyl carbonate, 10.35% methanol, 10% water and 34.43% acetic acid. The dimethyl carbonate conversion was 96.6%, and the net acetyl production rate was 2.5 moles/L catalyst-hour.

The carbonylation process was continued in this fashion for an additional 4 hours with the catalyst temperature at 197° C. (7° C. exotherm) to insure that the system was at steady state. The condensate (28.3 g) contained the following components: 9.51% methyl iodide, 0.01% acetone, 50.9% methyl acetate, 28.62 dimethyl carbonate, 12.31% methanol, 1.26% water and 2.08% acetic acid. The dimethyl carbonate conversion was 71.1% and the net acetyl production rate was 2.5 moles/L catalyst-hour. At this point in the experiment, with the feeds continuing while maintaining reactor temperature and pressure, a vent gas sample was taken from a tee in the line connecting the product collection tank and the backpressure regulator using a gas sampling bomb. The bomb was pressurized and vented three times with the vent gas from the reaction before the final pressurization to purge the system. The vent gas contained (by volume) 0.03% hydrogen, 0.07% oxygen, 0.62% nitrogen, 0.05% methane, 88.42% carbon monoxide and 10.72% carbon dioxide, demonstrating that the carbonylation process produces carbon dioxide.

Example 3

This example illustrates the formation of methyl acetate and acetic anhydride in the vapor phase over a catalyst dissolved in a non-volatile liquid. The example also shows the effect of adding small amounts of hydrogen to the carbon monoxide feed.

Carbon monoxide (20 SCCM) was fed to the reactor described in Example 2 to prevent the liquid components from running out through the frit in the base of the reactor. The reactor then was charged with 1-butyl-3-methylimidazolium iodide ionic liquid (14.45 g, 10 mL, 0.054 mole), and a solution of rhodium trichloride hydrate (83.7 mg, 40.01% Rh, 0.32 mmole) in methanol (5 mL) was added. Additional methanol (5 mL in portions) was used to rinse any residual rhodium solution into the reactor. The reactor was pressurized to 16.6 barg with carbon monoxide and then heated to 190° C. The carbon monoxide feed to the reactor was set for 120 SCCM. Prior to performing the dimethyl carbonate carbonylation, a methanol carbonylation and then a dimethyl ether carbonylation were performed under conditions similar to those used for the subsequent dimethyl carbonate carbonylation. As a result of these two preliminary reactions, the entire reactor system was free of methanol when the dimethyl carbonate carbonylation was started. A liquid mixture containing molar ratio=1.0 dimethyl carbonate/0.39 acetic acid/0.11 methyl iodide (density=1.127 g/mL) was fed to the vaporizer at 0.10 mL/minute along with the 120 SCCM carbon monoxide. The catalyst solution temperature rose and eventually leveled out at 193° C. Sample 1 (5.75 g) of the condensate was taken after one hour, and it contained the following components: 11.97% methyl iodide, 0.01% acetone, 31.55% methyl acetate, 0% dimethyl carbonate, 0% methanol, 0% water, 38.83% acetic acid, 14.86% acetic anhydride and 0.07% ethylidene diacetate. The dimethyl carbonate conversion was 100% and the net acetyl production rate was 6.05 moles/L catalyst solution-hour.

The experiment was continued for an additional hour, and sample 2 (5.84 g) of liquid condensate taken contained the following components: 12.65% methyl iodide, 0% acetone, 41.35% methyl acetate, 0% dimethyl carbonate, 0% methanol, 0% water, 33.09% acetic acid, 10.2% acetic anhydride and 0% ethylidene diacetate. The dimethyl carbonate conversion was 100%, and the net acetyl production rate was 5.85 moles/L catalyst solution-hour. The reaction was continued producing methyl acetate and acetic anhydride under these conditions for an extended period of time during which the catalyst activity appeared to decline slightly, level out and then increase slightly as shown in the following Table wherein Sampling Time is the hours under reaction conditions between samples and the Space Time Yield is the moles of acetyl produced per liter of catalyst solution per hour.

TABLE

| Sample Number | Sampling Time | Space Time Yield |
|---|---|---|
| 3 | 2.5 | 5.0 |
| 4 | 2 | 5.2 |
| 5 | 16 | 5.2 |
| 6 | 2 | 5.3 |
| 7 | 5 | 5.4 |

The feed gas producing samples 6 and 7 contained 6 SCCM hydrogen in addition to the 120 SCCM carbon monoxide.

The invention has been described in detail with particular reference to preferred embodiments thereof, but it will be understood that variations and modifications can be effected within the spirit and scope of the invention.

I claim:

1. Process for the co-production of carbon dioxide and a carbonyl compound selected from a carboxylic acid, an alkyl carboxylate ester, a carboxylic acid anhydride or a mixture of any two or more thereof which comprises contacting in a carbonylation zone a dialkyl carbonate with carbon monoxide in the presence of a metal carbonylation catalyst and a halide compound under carbonylation conditions of pressure and temperature.

2. Process according to claim 1 further comprising recovering the carbon dioxide by absorption.

3. Process according to claim 2 wherein the absorption comprises contacting the carbon dioxide with a solvent selected from primary and secondary amino alcohols containing a total of up to 10 carbon atoms, methanol, propylene carbonate, dimethyl ethers of polyethylene glycol of two to twelve glycol units, n-methyl-pyrrolidone, and sulfolane.

4. Process according to claim 1 wherein the process is carried out at a temperature of about 100 to 300° C. and a total pressure of about 0.1 to 500 bars absolute in the presence of a Group VIII metal carbonylation catalyst and a halide compound selected from hydrogen halides and alkyl halides containing 1 to 6 carbon atoms wherein the halide is chloride, bromide or iodide.

5. Process according to claim 1 wherein the process is carried out at a temperature of about 100 to 220° C. and a total pressure of about 0.1 and 100 bars absolute in the presence of a metal carbonylation catalyst selected from rhodium, iridium and compounds thereof and a halide compound selected from hydrogen iodide and alkyl iodides containing 1 to 6 carbon atoms.

6. Process for the co-production of carbon dioxide and a carbonyl compound selected from a carboxylic acid, an alkyl carboxylate ester, a carboxylic acid anhydride or a mixture of any two or more thereof which comprises contacting in the liquid phase in a carbonylation zone a dialkyl carbonate with carbon monoxide in the presence of a metal carbonylation catalyst and a halide compound under carbonylation conditions of pressure and temperature.

7. Process according to claim 6 further comprising recovering the carbon dioxide by absorption.

8. Process according to claim 6 wherein the process is carried out at a temperature of about 100 to 300° C. and a total pressure of about 0.1 to 500 bars absolute in the presence of a Group VIII metal carbonylation catalyst and a halide compound selected from hydrogen halides and alkyl halides containing 1 to 6 carbon atoms wherein the halide is chloride, bromide or iodide.

9. Process according to claim 6 wherein the process is carried out at a temperature of about 100 to 220° C. and a total pressure of about 1 to 80 bars absolute in the presence of a metal carbonylation catalyst selected from rhodium, iridium and compounds thereof and a halide compound selected from hydrogen iodide and alkyl iodides containing 1 to 6 carbon atoms.

10. Process according to claim 6 wherein the process is carried out at a temperature of about 150 to 200° C. and a total pressure of about 3 to 70 bars absolute in the presence of a metal carbonylation catalyst selected from rhodium, iridium and compounds thereof and a halide compound selected from hydrogen iodide and alkyl iodides containing 1 to 6 carbon atoms.

11. Process for the co-production of carbon dioxide and a carbonyl compound selected from acetic acid, methyl acetate, acetic anhydride or a mixture of any two or more thereof which comprises contacting in the liquid phase in a carbonylation zone dimethyl carbonate with carbon monoxide in the presence of a metal carbonylation catalyst selected from rhodium, iridium and compounds thereof and methyl iodide at a temperature of about 100 to 220° C. and a total pressure of about 1 to 80 bars absolute.

12. Process for the co-production of carbon dioxide and a carbonyl compound selected from a carboxylic acid, an alkyl carboxylate ester, a carboxylic acid anhydride or a mixture of any two or more thereof which comprises contacting in the vapor phase in a carbonylation zone a dialkyl carbonate with carbon monoxide in the presence of a metal carbonylation catalyst and a halide compound under carbonylation conditions of pressure and temperature.

13. Process according to claim 12 further comprising recovering the carbon dioxide by absorption.

14. Process according to claim 12 wherein the process is carried out at a temperature of about 150 to 300° C. and a total pressure of about 1 to 50 bars absolute in the presence of a Group VIII metal carbonylation catalyst and a halide compound selected from hydrogen halides and alkyl halides containing 1 to 6 carbon atoms wherein the halide is chloride, bromide or iodide.

15. Process according to claim 12 wherein the process is carried out at a temperature of about 100 to 220° C. and a total pressure of about 1 to 80 bars absolute in the presence of a metal carbonylation catalyst selected from rhodium, iridium and compounds thereof and a halide compound selected from hydrogen iodide and alkyl iodides containing 1 to 6 carbon atoms.

16. Process according to claim 12 wherein the process is carried out at a temperature of about 170 to 250° C. and a total pressure of about 3 to 30 bars absolute in the presence of a metal carbonylation catalyst selected from rhodium, iridium and compounds thereof and a halide compound selected from hydrogen iodide and alkyl iodides containing 1 to 6 carbon atoms.

17. Process according to claim 16 wherein the process is carried out in the presence of a metal carbonylation catalyst selected from compounds of rhodium and iridium dissolved in a non-volatile solvent.

18. Process according to claim 16 wherein the process is carried out in the presence of a mixture of a metal carbonylation catalyst selected from rhodium and iridium deposited on an inert catalyst support material in a non-volatile solvent.

19. Process for the co-production of carbon dioxide and a carbonyl compound selected from acetic acid, methyl acetate, acetic anhydride or a mixture of any two or more thereof which comprises contacting in the vapor phase in a carbonylation zone dimethyl carbonate with carbon monoxide in the presence of a metal carbonylation catalyst selected from rhodium, iridium and compounds thereof and methyl iodide at a temperature of about 170 to 250° C. and a total pressure of about 3 to 30 bars absolute.

20. Process according to claim 19 further comprising recovering the carbon dioxide by absorption.

21. Process according to claim 19 wherein the process is carried out in the presence of a metal carbonylation catalyst selected from compounds of rhodium and iridium dissolved in a non-volatile solvent.

22. Process according to claim 19 wherein the process is carried out in the presence of a mixture of a metal carbonylation catalyst selected from rhodium and iridium deposited on an inert catalyst support material in a non-volatile solvent.

* * * * *